(12) United States Patent
Arafat et al.

(10) Patent No.: US 7,629,004 B2
(45) Date of Patent: *Dec. 8, 2009

(54) COMPOSITION AND PROCESS FOR REMOVING AND PREVENTING MILDEW AND FUNGAL GROWTH

(75) Inventors: El Sayed S. Arafat, Leonardtown, MD (US); Craig A. Matzdorf, California, MD (US); Stephen J. Spadafora, LaPlata, MD (US); David L. Gauntt, St. Leonard, MD (US); Paul R. Roser, Leonardtown, MD (US); James A. Whitfield, Newport, NC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 360 days.

This patent is subject to a terminal disclaimer.

(21) Appl. No.: 11/703,906

(22) Filed: Jan. 31, 2007

(65) Prior Publication Data

US 2008/0031974 A1    Feb. 7, 2008

Related U.S. Application Data

(62) Division of application No. 11/151,170, filed on Jun. 10, 2005, now Pat. No. 7,494,670.

(51) Int. Cl.
*A01N 39/00* (2006.01)
*A01N 31/14* (2006.01)
*A01N 43/38* (2006.01)
*A01N 43/50* (2006.01)
*A01N 43/52* (2006.01)
*A01N 43/64* (2006.01)
*A01N 43/76* (2006.01)
*A01N 59/00* (2006.01)
*A01N 59/14* (2006.01)
*C11D 3/08* (2006.01)
*C11D 3/395* (2006.01)

(52) U.S. Cl. ........... 424/613; 424/615; 424/657; 424/722; 424/126; 510/199; 510/334; 510/378; 510/421; 514/359; 514/375; 514/394; 514/396; 514/415; 514/717

(58) Field of Classification Search ........ 424/613, 424/615, 657, 722; 510/199, 334, 378, 421; 514/359, 375, 394, 396, 415, 717
See application file for complete search history.

(56) References Cited

U.S. PATENT DOCUMENTS 3,723,347 A * 3/1973 Mitchell ............ 252/389.22
6,235,124 B1 * 5/2001 Rubin ..................... 134/26
7,494,670 B2 * 2/2009 Arafat et al. ........... 424/613

OTHER PUBLICATIONS

P. G. Cao, J. L. Yao, J. W. Zheng, R. A. Gu and Z. Q. Tian, "Comparative study of inhibition effects of benzotriazole for metals in neutral solutions as observed with surface-enhanced Raman spectroscopy", Langmuir, 2002, 18, 100-104.*

* cited by examiner

*Primary Examiner*—Johann R Richter
*Assistant Examiner*—Nathan W Schlientz
(74) *Attorney, Agent, or Firm*—Mark O. Glut; Mark D. Kelly

(57) ABSTRACT

This invention comprises a composition and the process of using the composition for removing and preventing mold, mildew, and fungal growth. The composition comprises at least one alkali metal perborate, at least one inhibiting compound selected from the group consisting of alkali metal silicates, triazoles and mixtures thereof in any ratio, at least one corrosion inhibitor, and effective amounts of surfactant.

5 Claims, 3 Drawing Sheets

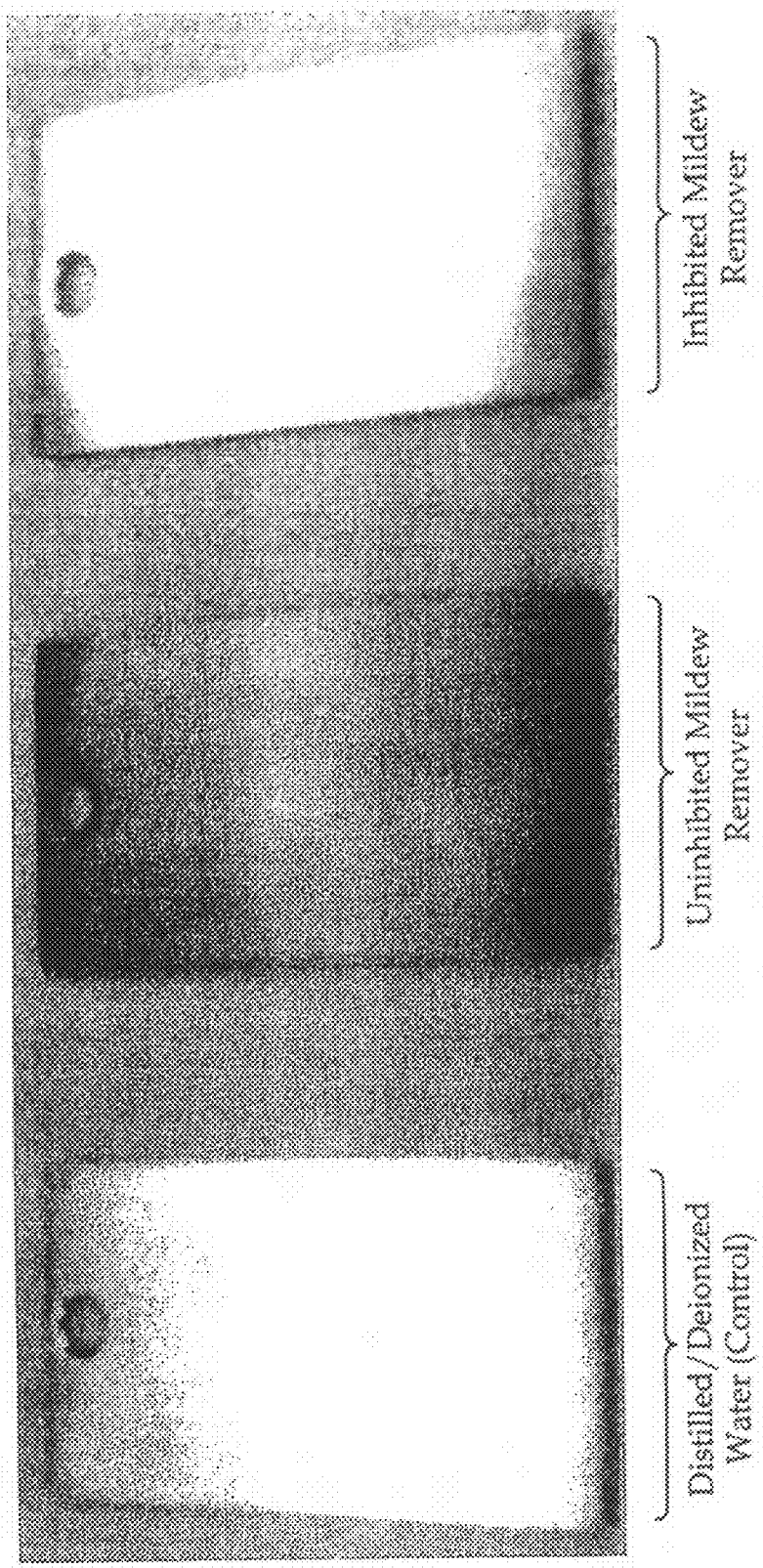

COMPOSITION AND PROCESS FOR REMOVING AND PREVENTING MILDEW AND FUNGAL GROWTH

CROSS REFERENCES

This application is a division of application Ser. No. 11/151,170, now U.S. Pat. No. 7,494,670 filed Jun. 10, 2005, entitled Composition and Process for Removing and Preventing Mildew and Fungal Growth.

ORIGIN OF INVENTION

The invention described herein was made by employee(s) of the United States Government and may be manufactured and used by or for the Government for governmental purposes without the payment of any royalties thereon or therefore.

BACKGROUND OF THE INVENTION

Field of the Invention

This invention relates to compositions and to a process for using said compositions for removing and preventing mildew, mold and fungal growth on various surfaces. In many geographical regions, the unwanted growth of mold and mildew is a serious problem. The rapid growth of mold and mildew on metal surface is a serious problem in humid geographical areas. Mildew growth on the interior of aircraft surfaces, and particularly aircraft operated in humid climates is even more of a serious problem. The buildup of mildew causes corrosion and operational damage to the aircraft in addition to creating potential health hazards to flight crews and maintenance personnel. Present methods of removing mold and mildew are time consuming and inadequate and have caused corrosion when applied to metal substrates such as aircraft interior surfaces and the like.

SUMMARY OF INVENTION

This invention relates to compositions and to the process of using the compositions for removing and preventing mold, mildew and fungal growth on various surfaces. The composition comprises an aqueous solution having a pH ranging from 7.0 to 10 and contains from about 0.1 to 3.0 percent by weight of at least one alkali metal perborate, from about 0.05 to 5.0 percent by weight of one or more inhibiting compound selected from the group consisting of alkali metal silicates, triazoles such as benzotriazole and mixtures of said silicates and triazoles in any ratio. In addition, the aqueous solutions contain from about 0.0 to 3.0 percent by weight of at least one water soluble corrosion inhibitor selected from the group consisting of benzimidazoles, benzazoles and benzoxazoles, and from about 0.0 to 5.0 percent by weight of at least one water soluble surfactant.

FIGS. 1-3 show the test results of the original mildew remover of Example 1 in comparison to the mildew remover of Examples 2 and 3 of this invention.

Therefore, it is an object of this invention to provide an effective, noncorrosive mildew inhibitor and remover for aircraft application.

It is another object of this invention to provide an effective noncorrosive mildew inhibitor and remover having performance characteristics required by standard tests in military specifications.

It is another object of this invention to provide an effective noncorrosive mildew inhibitor and remover capable of passing the sandwich corrosion and the immersion corrosion test.

These and other objects of this invention will become apparent by reference to the detailed description when considered in conjunction with the accompanying FIGS. 1, 2, and 3, (photos).

BRIEF DESCRIPTION OF THE DRAWINGS

FIG. 3 (photo) shows total immersion corrosion test for titanium alloy (Ti 6Al 4V) in uninhibited (Example 1) and inhibited (Examples 2 and 3) mildew remover solutions (ASTM F483).

Figure 1:
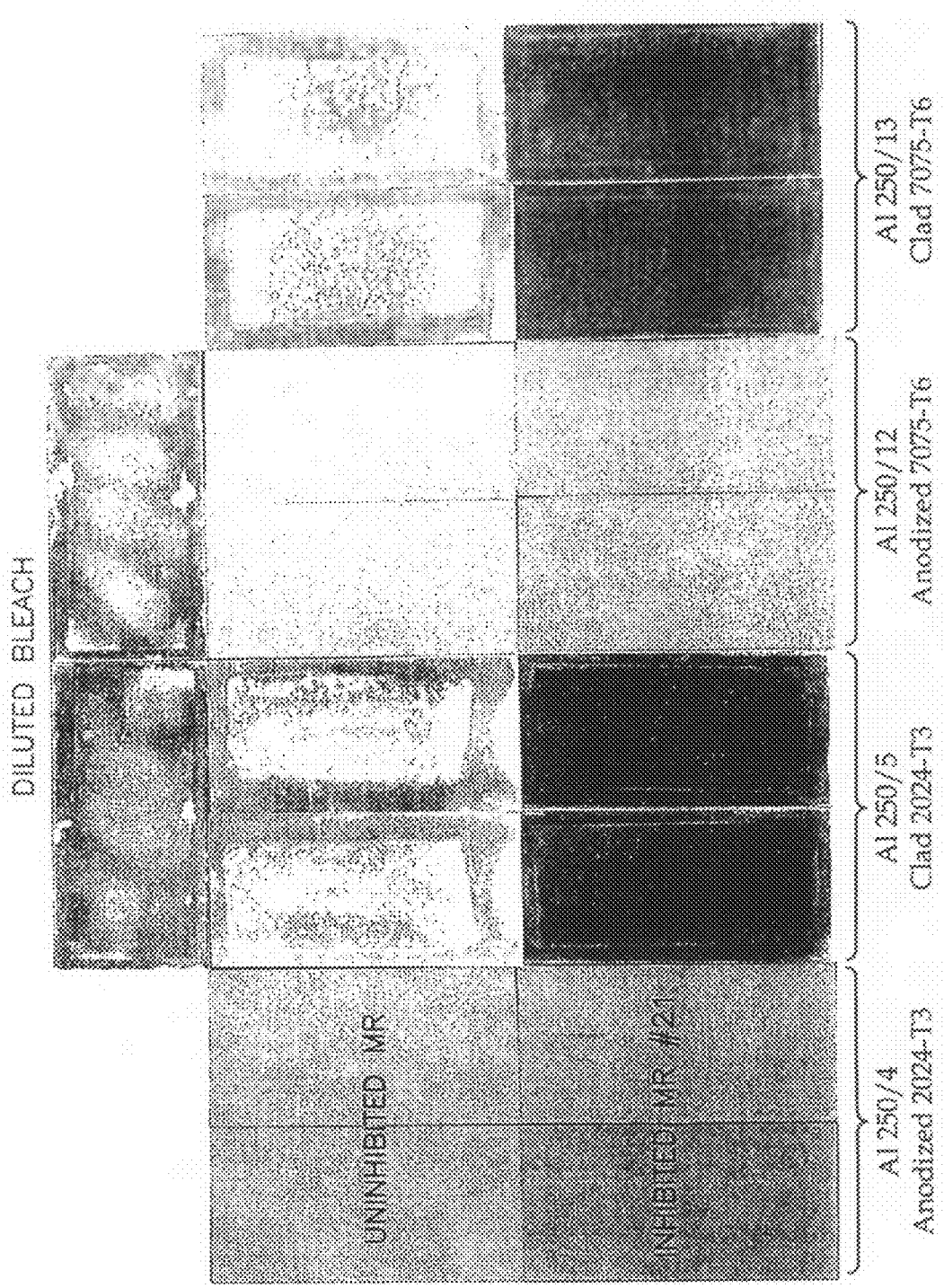
FIG. 1 (photo) shows sandwich corrosion test for the uninhibited (Example 1) and the inhibited mildew (Example 2 and 3) remover cleaner (ASTM F1110).

More specifically, maintenance procedures to remove mold, mildew growth and mildew staining from aircraft parts have historically required many man-hours. In addition, previously approved materials were often inadequate. The use of unauthorized cleaning solutions, such as household chlorine bleach (sodium hypochlorite), can induce corrosion damage to critical metallic surfaces. In addition, chlorine bleach causes environmental concerns. Results of fungal degradation studies of polymeric materials used in Navy aircraft showed that the approved military cleaning procedure, based on isopropyl alcohol, was ineffective; see: B. Little, R. Ray and J. Lee, "An Overview of Microbiologically Influenced Corrosion In Aircraft", Naval Research Laboratory, Stennis Space Center, Technical Report No. A709314, (1997), and D. Lavoie, B. Little, R. Ray, K. Hart, P. Wagner, "Microfungal degradation of Polyurethane Paint and Corrosion of Aluminum Alloys in Military Helicopters," in the Corrosion Proceeding, of the National Association of Corrosion Engineers, International Corrosion/97, paper No. 218, Houston, Tex., (1997). Environmental Scanning Electron Microscopy (ESEM) micrographs indicated that surface cleaning only removes spores from the ends of the mildew hyphae, but fragments of the hyphae remained and re-grow as soon as conditions are favorable. Even through interior surfaces appear clean, they are still contaminated with fungi. In addition, fungi appear to be able to use certain operational fluids, such as hydraulic fluid (MIL-PRF-83282) and corrosion preventive compounds (CPCs) as nutrients.

A study of fungal contamination on the interior surface of H-46 and H-53 rotary-wing aircraft at Naval Air Depot, Cherry Point, N.C., isolated eight genera of microfingi; see: Lavoie, M. D., Little, B. J., "Fungal Contamination of H-53 Aircraft", Naval Research Laboratory, Stennis Space Center, Technical Report NRL/MR/7333-96-7725, (1996). The study indicated that some corrosion on unprotected aluminum surface can be attributed to bacterial and fungal growth. One of the isolated fungi (Aureobasidium) from the H-53 is known to cause superficial discoloration on latex paint; see Zabel, R. A. and Terracina, F., "The role of *Aureobasidium Pullulans* in the disfigurement of latex paints", Development in Industrial Microbiology, vol. 21, pages 179-190, (1980). Another report indicated that one microfungus (*Cladosporium*) similar to the one found on H-53, is capable of corroding 2024 aluminum alloy panels by producing acidic metabolic products; see Videla, H., "The action of *Cladosporium resinae* growth on the electrochemical behavior of aluminum", Biologically Induced Corrosion, Proceedings of the International Conference on Biologically induced Corrosion, Dexter, S.C. (ed). National Association of Corrosion Engineers (NACE), Houston, Tex. Pages 215-222, (1986). An additional study by Salvarezza and Videla has shown that fungi are known to thrive at the oil-water interface to produce acids that can corrode metals; see Salvarezza, R. C., and Videla, H. A., "Microbiological corrosion in fuel storage tanks, Part 1: anodic behavior", Acta Cientifica Venezulan, vol. 35, pages 244-247, (1984).

To mitigate these problems, a novel mildew composition was developed by National Air Depot Cherry Point personnel. The original mildew remover formula comprises an aqueous solution consisting of sodium perborate and nonionic detergents; see U.S. Pat. No. 6,235,124 (Method and Solution for Removal of Mildew, May 22, 2001, Lynn Rubin) and U.S. Pat. No. 6,655,527 (Kit for Removing Mildew, Dec. 2, 2003, Lynn Rubin), the disclosures of which are hereby incorporated by reference. However, the ingredients must be mixed immediately prior to use, as the solution becomes ineffective after about twenty-four hours. The product is applied with clean cheesecloth or a soft bristle brush to mildew growth and allowed to remain for about 5 to 15 minutes. The surface is then cleaned thoroughly with fresh water to rinse away residue.

The patented mildew remover was evaluated to determine the effects on aircraft materials using selected tests from MIL-PRF-85570D and ADS-61A-PRF-2002 (aircraft cleaning) specifications, the disclosures of which are hereby incorporated by reference. The mildew remover was tested in diluted concentrations to simulate rinse residues. Testing was initiated after aging the mixed product for up to about 96 hours to determine the composition's activity period. After completing the initial tests, the above-identified patented mildew remover caused some corrosion in both the sandwich corrosion and the total immersion corrosion tests on titanium alloy (Ti 6Al 4V). As a result of the test, the mildew remover was modified, by incorporating various corrosion inhibitors to mitigate corrosion while maintaining composition performance. Inhibited formulations were subjected to selected tests in Navy MIL-PRF-85570D and Army ADS-61A-PRF-2002 cleaner specifications, and adjusted as necessary. The best formulation was tested to the requirements of the two specifications stated above and then field-tested to validate mildew removing performance. The test methods were taken from the MIL-PRF-85570D and ADS-61A-PRF-2002 specifications as follows:

1. pH Value (ASTM E70-02)
2. Hydrogen Embrittlement as per ASTM F519-97
3. Sandwich Corrosion Test (ASTM F1110-02)
4. Cadmium Corrosion Test (ASTM F1111-98)
5. Total Immersion Corrosion (ASTM F483-02)
6. Effect on Polyimide Wire
7. Effect on Painted Surfaces (ASTM F502-02)
8. Effect on Plastics (ASTM F484-02)
9. Stress Corrosion on Titanium (ASTM F945-01)
10. Sealant Adhesions, Paint Adhesion, and Adhesive Bonding (ADS-61-PRF-2002)
11. Field Test for the inhibited mildew remover formulations In addition to testing the full strength mildew remover to the listed tests, dilutions of 50%, 25% and 10% were tested for sandwich corrosion to simulate the consequences of incomplete rinsing. Aged samples of the mixed product were evaluated in the sandwich corrosion test to determine the window of activity of the mixed product. The sandwich corrosion test was performed in accordance with ASTM F 1110 using deionized/distilled water as a control. The test was performed on four aluminum alloy coupons: anodized aluminum 2024-T3 (SAE-AMS-QQ-A-250/4), Alclad 2024-T3 (SAE-AMS-QQ-A-250/5), anodized aluminum 7075-T6 (SAE-AMS-QQ-A-250/12). and Alclad 7075-T6 (SAE-AMS-QQ-A-250/13). Aluminum coupons were sandwiched together with filter paper saturated with mildew remover between the coupons. The sandwiched coupons were cycled between warm dry air (38° C.) and warm humid air (relative humidity 100%) for 7 days. Sandwich corrosion testing was performed using diluted chlorine bleach solution, Reagent Water (ASTM D1193), a 1.5% Sodium Perborate solution, and a series of perborate and surfactant solutions with various corrosion inhibitors in several concentrations. Inhibitors tested include Zinc Borate, Sodium Dichromate, Monacor 4000, Benzotriazole, Sodium Silicate "N", Sodium Benzoate, Sodium Orthosilicate, Sodium Metasilicate, Cobratec TT-50-S, Sodium Nitrite, 2-Mercaptobenzimidazole, and 2-Mercaptobenzoxazole.

Table 3 details the combination of inhibitors investigated and the subsequent sandwich corrosion test results. The test results are shown in Tables 1 and 2 and in FIGS. 1 and 2. The original mildew remover showed surface corrosion and pitting corrosion on all coupons except anodized 7075-T6 (250/12). The distilled water did not show any corrosion on aluminum coupons, except for some staining which appeared on the anodized 2024-T3 (250/4) coupons. The test was performed twice with Whatman filter paper #4 and once with Whatman Glass Microfiber. Overall performance is detailed as follows:

The original mildew remover formulation (Example 1) failed the sandwich corrosion test, as required by the MIL-PRF-85570D and ADS 61A-PRF-2002 specifications as follows:

a. Dilutions of the original mildew remover (50%, 25% and 10% concentration) proved corrosive beyond the specification limits and pitting was observed.

b. Samples made using 24-hour-old solution (uninhibited formula) were found to fail sandwich corrosion testing.

c. Samples made using 96-hour-old solution (uninhibited formula) were found to be comparable to the control.

d. Samples tested at the prescribed temperature of 100° F. showed more pitting than those tested at 72° F.

e. Samples made using tap water in place of reagent water failed with ratings of #4 for corrosion pitting.

The mildew remover formulation (Example 2) passed the sandwich corrosion test, in accordance with the MIL-PRF-85570D and ADS-61A-PRF-2002 specification requirements.

The following examples illustrate the aqueous solutions of this invention, and the method of using the basic solutions for removing and inhibiting the growth of mold and mildew on various surfaces and particularly metal surfaces.

EXAMPLE 1

The original Mildew Remover (M.R.) Formulation (uninhibited) consists of the following compounds in an aqueous solutions:
Sodium Perborate Monohydrate, 1.5% by weight
Triton X-100 surfactant, 0.39% by weight
Reagent Water (ASTM D1193)

EXAMPLE 2

Inhibited Mildew Remover (M.R.) consists of the following compounds in an aqueous solution:
Sodium Perborate Monohydrate, 1.5% by weight
Triton X-100 surfactant, 0.39% by weight (octylphenoxypolyethoxyethanol)
Sodium Silicate N, 0.5% by weight
Benzotriazole, 0.25% by weight
Reagent Water (ASTM D1193)

EXAMPLE 3

Inhibited Mildew Remover consists of the following compounds in solution:
Sodium Perborate Monohydrate, 1.5% by weight
5 Triton X-100 surfactant, 0.39% by weight (octylphenoxypolyethoxyethanol)
Sodium Silicate N, 0.5% by weight
2-Mercaptobenzimidazole, 0.25% by weight
Reagent Water (ASTM D1193)

EXAMPLE 4

| Aqueous Compositions | Percent by Weight |
|---|---|
| Alkali Metal Perborates | 0.1 to 3.0 |
| (Sodium and/or Potassium Perborates) | 1.0 to 2.0 |
| Inhibiting compounds | 0.05 to 5.0 |
| (Silicates and triazoles) | 0.1 to 2.0 |
| Corrosion Inhibitors | 0.0 to 3.0 |
| (Benzimidazoles, benzazoles, benzoxazoles) | 0.1 to 2.0 |
| Surfactants | 0.0 to 5.0 |
| (non-ionic, cationic, anionic) | 0.1 to 2.0 |

Figure 2:
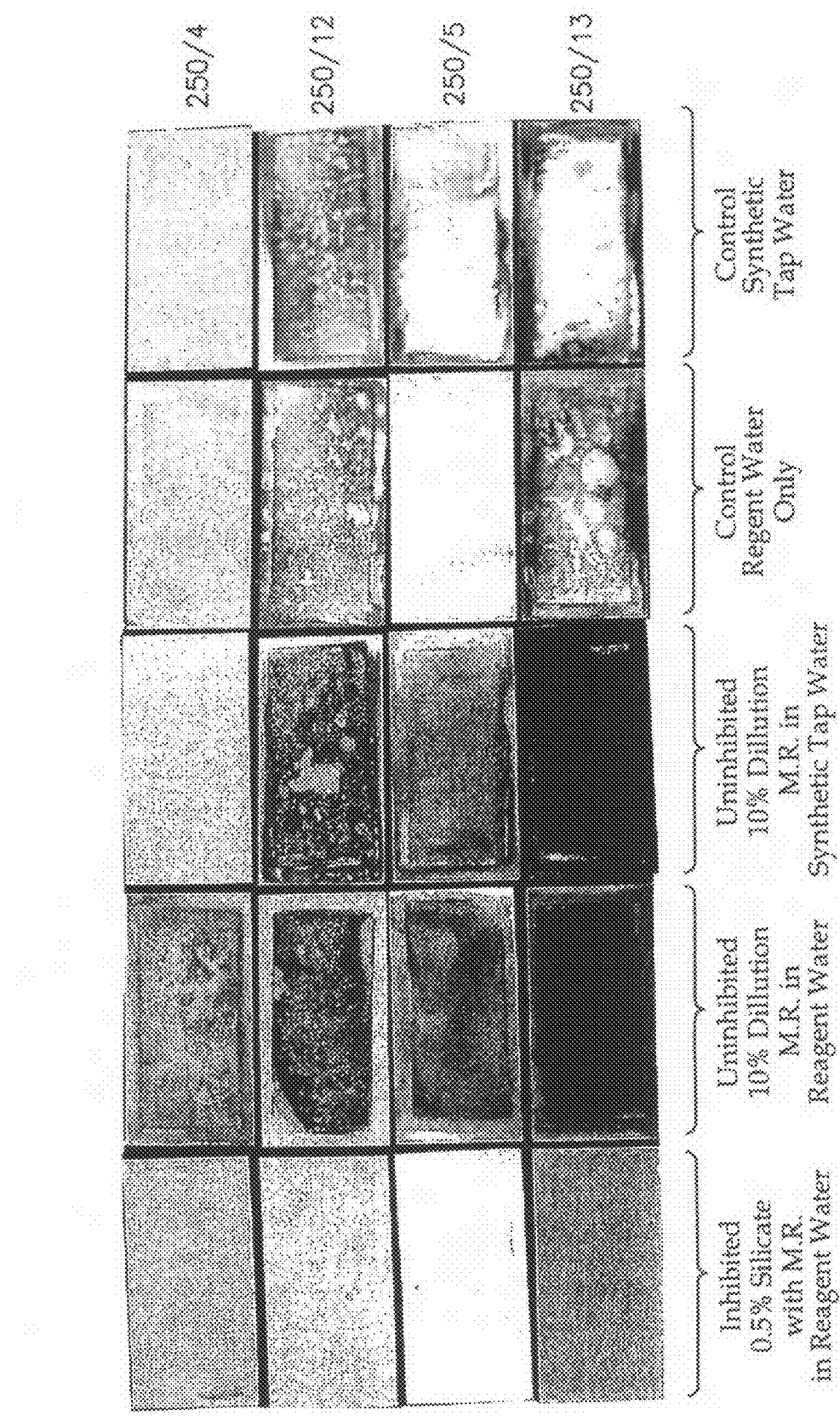
FIG. 2 (photo) shows the sandwich corrosion test results for the inhibited (Examples 2 and 3) and the uninhibited (Example 1) mildew remover in severe corrosion conditions (humidity chamber).

Total Immersion Corrosion Test: The total immersion corrosion test was performed in accordance with ASTM F483. The selected metal alloys were immersed in the mildew remover solution for seven days at 100° F. The weight change of each specimen was calculated, and the specimen was examined for visual evidence of corrosion. The weight changes for the selected metal alloys are listed in Table 1. The selected metal alloys met the test requirements except the Ti 6Al 4V alloy which showed a dark purple color as shown in FIG. 3. This dark purple color is an indication of the oxidation of vanadium in the alloy to vanadium oxide. The inhibited mildew remover formulas of Example 2 and 3 did not yield the dark purple color on titanium and met the requirements of the total immersion corrosion test. Various inhibitors for the mildew remover were tested that did not achieve the optimum result or were not environmentally acceptable, see Table 3. Sandwich Corrosion testing was performed using diluted chlorine bleach solution, Reagent Water (ASTM D1193), Synthetic Tap Water (MIL-C-85570), a 1.5% sodium perborate solution, and a series of perborate and surfactant solutions with various corrosion inhibitors in several concentrations. Inhibitors tested include Zinc Borate, Sodium Dichromate, Monacor 4000, Benzotriazole, Sodium Silicate "N", Sodium Benzoate, Sodium Orthosilicate, Sodium Metasilicate, Cobratec TT-50-S, Sodium Nitrite, 2-Mercaptobenzimidazole, and 2-Mercaptobenzoxazole. Table 3 details the combination of inhibitors investigated and the subsequent sandwich corrosion test results. Screening of the inhibitors showed that various combinations worked for some substrates, but only the formulation of Examples 2 and 3 passed both the MIL-PRF-85570D and ADS-61-A-PRF-2002 requirements of having no rating greater than #1 or no greater than the control rating in the sandwich corrosion test as shown in FIGS. 1 and 2 and Table 3.

The alkali metal perborates of this invention and preferably the sodium and potassium perborates are added to the aqueous solutions in amounts ranging from about 0.1 to 3.0 percent by weight and preferably in amounts ranging from about 1.0 to 2.0 percent by weight of the solutions. To obtain maximum performance in preventing and removing mold and mildew growth on metal surfaces such as aluminum, the inhibiting compounds i.e. the alkali metal silicates such as sodium and potassium silicates and the triazoles are added to the aqueous solution in amounts ranging from about 0.05 to 5.0 percent and preferably in amounts ranging from about 0.1 to 2.0 percent by weight of the solution. These inhibiting compounds are selected from the group consisting of alkali metal silicates and triazoles such as benzotriazole or tolyltriazol and various mixtures of said silicates and triazoles in any ratio.

In preparing the anti-mildew or inhibiting solutions of this invention, known water soluble surfactants are added to the solutions in amounts ranging from about 0.0 to 5.0 percent by weight and preferably from 0.1 to 2.0 or from about 0.1 to 1.0 percent by weight. The surfactants are added to the aqueous solution to provide better wetting properties by lowering the surface tension thereby insuring complete coverage and a more uniform film on the metal substrates. The surfactants include at least one water soluble compound selected from the group consisting of non-ionic, anionic, and cationic surfactants. Some of the water soluble surfactants include monocarboxylimidoazoline, alkylsulfate sodium salts (DUPONOL®), salts of alkylbenzene sulfonates, ethoxylated or propoxylated alkylphenols (IGEPAL®), alkylsulfonamides, alkaryl sulfonates, palmiticalkanol amides (CENTROL®), the alkylarylpolyether alcohols such as octylphenylpolyethoxy ethanol or polyoxyethylene nonylphenyl ether, (TRITON®), sorbitan monopalmitate (SPAN®), dodecylphenyl polyethyleneglycol ether (TERGITOL®), alkyl pyrrolidones, polyalkoxylated fatty acid esters, lower alkylbenzene sulfonates and various mixtures of these surfactants.

The preferred corrosion inhibitors added to the solutions of this invention are water-soluble compounds selected from the group consisting of benzimidazoles, benzazoles, benzoxazoles and mixtures of these corrosion inhibitors in any ratio. The corrosion inhibitors are dissolved in the aqueous solutions, having a pH ranging from 7.0 to 10, in amounts ranging from about 0.0 to 3.0 percent by weight and preferably in amounts ranging from about 0.1 to 2.0 percent by weight of the solution. The preferred inhibitor compounds in addition to the silicates include triazoles containing up to 12 carbon atoms. The preferred aryl triazoles contain from 6-10 carbon atoms, including compounds such as benzotriazole and tolyltriazole. The aryl triazoles are commercially available under the trade name "COBRATEC".

An embodiment of the process of inhibiting and removing mold, mildew and fungal growth from metal surfaces of this invention includes treating the metal surfaces with an aqueous solution consisting essentially of from about 0.1 to 3.0 percent by weight of sodium and/or potassium perborate monohydrate; from about 0.05 to 5.0 percent by weight of at least one alkali metal silicate; a member selected from the group consisting of (i) benzotriazole, tolyltriazole, or a mixture thereof, and (ii) from about 0.1 to 2.0 weight percent of at least one water soluble corrosion inhibitor selected from the group consisting of benzimidazoles, benzazoles, and benzoxazoles; and 0.1 to 5.0 percent by weight of at least one water soluble surfactant; wherein the aqueous solution has a pH ranging from 7.0 to 10, does not include a chlorine bleach, and when benzotriazole, tolyltriazole, or a mixture thereof is present in the aqueous solution the combined amount of alkali metal silicate and benzotriazole, tolyltriazole, or a mixture thereof does not exceed about 5.0 percent by weight of the solution.

As shown, a combination of inhibitors e.g. silicates and triazoles was developed to eliminate the corrosion problems associated with the original (Example 1) mildew remover formula. The inhibited mildew remover formula eliminates the corrosion problem associated with aluminum alloys in the sandwich corrosion test as seen in FIGS. 1 and 2. In addition, the inhibited mildew remover formula eliminated the problem associated with titanium alloys in the total immersion corrosion test as shown in FIG. 3. The inhibited mildew remover formula also protects against potential damage caused by the oxidative effect of the uninhibited formula on aircraft metals. These factors were taken in consideration with all other precautions normally taken to minimize the damage potential of the instant composition in the Standard Depot Level Maintenance (SDLM) procedures. The cleaning efficiency test results were satisfactory on both the original and inhibited formulations.

Table 1 is an evaluation of the uninhibited and inhibited mildew remover in accordance with MIL-PRF-85570D (Cleaning Compounds, Aircraft Exterior).

TABLE 1

| Requirements | Specification Limits | | Uninhibited Mildew Remover | Inhibited Mildew Remover |
|---|---|---|---|---|
| pH (ASTM E70) | 7-10 | | 10.31-10.48 | 9.98 |
| Sandwich Corrosion Test (ASTM F1110) | Not more than distilled water | | Failed Al 250/5 Al 250/13 Al 250/4 | Pass |
| Total Immersion Corrosion Test (ASTM F483) | No Visible Corrosion mg/cm$^2$/day | | Mg/cm$^2$/day | Mg/cm$^2$/day |
| | Al 7075 (250/12) | 0.04 | <0.01 | <0.01 |
| | Steel 1020 (AMS 5046) | 0.04 | <0.01 | <0.01 |
| | Ti 6Al 4V (AMS 9046) | 0.04 | <0.01 Purple Color | <0.01 |
| | Mg AZ31B (AMS4377) | 0.20 | 0.02 | 0.02 |
| Cadmium Corrosion (ASTM F1111) | Mg/cm$^2$/day | 0.20 | <0.01 | <0.01 |
| Hydrogen Embrittlement (ASTM F519 1a) | No Failure to 150 hr when loaded at 45% | | Pass | Pass |
| Effect on Plastics (ASTM F484) | Acrylic Type A No Crazing - 8 hrs | | Pass | Pass |
| | Acrylic Type C No Crazing - 8 hrs | | Pass | Pass |
| | Polycarbonate MIL-P-83310 - 2 hrs | | Pass | Pass |
| Effect on Painted Surfaces (ASTM F502) | No Softening >1 Pencil Hardness | | Pass | Pass |
| Effect on Polyimide Wire | No Dielectric Leakage No Physical Effect > Dist. Water | | Pass | Pass |

Table 2 shows the evaluation of uninhibited and inhibited mildew remover in accordance with ADS-61A-PRF-2002 (Army Aircraft Cleaner).

TABLE 2

| Requirements | Specification Limits | | Uninhibited Mildew Remover | Inhibited Mildew Remover |
|---|---|---|---|---|
| Sandwich Corrosion Test (ASTM F1110) | Not more than distilled water | | Failed Al 250/5 Al 250/13 Al 250/4 | Pass |
| Total Immersion Corrosion Test (ASTM F483) | No Visible Corrosion mg/cm$^2$/168 hr | | Pass Except Titanium (Per Table 1) | Pass |
| | Al 7075 (250/12) | 0.49 | | |
| | Steel 1020 (AMS 5046) | 0.49 | | |
| | Ti 6Al 4V (AMS 9046) | 0.35 | | |
| | Mg AZ31B (AMS4377) | 0.70 | | |
| Stress Corrosion | No Cracks in Table II Metals | | Pass | Pass |
| Hydrogen Embrittlement (ASTM F519 1a) | No Failure to 150 hr when loaded at 45% | | Pass | Pass |
| Effect on Plastics (ASTM F484) | Acrylic Type A No Crazing - 8 hrs | | Pass | Pass |
| | Acrylic Type C No Crazing - 8 hrs | | Pass | Pass |
| | Polycarbonate MIL-P-83310 - 2 hrs | | | Pass |
| Effect on Painted Surfaces (ASTM F502) | No Softening >1 Pencil Hardness | | Pass | Pass |
| Effect on Polyimide Wire | No Dielectric Leakage No Physical Effect > Dist. Water | | Pass | Pass |
| Sealant Adhesions | 100% Cohesive Failure 3.5 kN/m | | Primer Conforms Topcoat Failed Control and Cleaner | Primer Conforms Topcoat Failed Control and Cleaner |
| Adhesive Bonding | Meet or Exceed Control Methylethyl ketone | | Primer Conforms Topcoat Failed Control and Cleaner | Primer Conforms Topcoat Failed Control and Cleaner |

TABLE 3

ASTM F1110-02 Sandwich Corrosion Test Ratings

| Formula Number | Formulation | 250/4 Anodized | 250/5 Clad | 250/12 Anodized | 250/13 Clad |
|---|---|---|---|---|---|
| Control | Reagent Water | 1-2 | 1 | 1 | 1 |
| Formula #1 | Standard Formulation (Example 1) | 3-4 | 3-4 | 0-1 | 4 |
| Formula #2 | Standard Formula Plus 0.1% Zinc Borate | 2 | 1-2 | 1 | 3-4 |
| Formula #3 | Standard Formula Plus 0.1% Sodium Dichromate | 1 | 1 | 1 | 1 |
| Formula #4 | Standard Formula Plus 0.2% Sodium Dichromate | 1 | 1 | 1 | NR |
| Formula #5 | Standard Formula Plus 0.1% Benzotriazole | 1 | 1 | 1 | 2 |
| Formula #6 | Standard Formula Plus 0.25% N Sodium Silicate | 1-2 | 1-2 | 1 | 1 |
| Formula #7 | Standard Formula Plus 0.5% N Sodium Silicate | 1 | 1 | 1 | NR |
| Formula #8 | Standard Formula Diluted to 10% Concentration | 1 | NR | 4 | 3-4 |
| Formula #9 | Standard Formula Diluted to 25% Concentration | 1-2 | 2 | 2 | 1-2 |
| Formula #10 | Standard Formulation Diluted to 50% Concentration | 1 | 2 | 1 | 2-3 |
| Formula #11 | Standard Formula Plus 0.25% Sodium Benzoate | 1 | 2 | 1 | NR |
| Formula #12 | Standard Formula Plus 0.5% Sodium Benzoate | 1-2 | 2-4 | 1 | 2-4 |
| Formula #13 | Standard Formula Plus 0.25% Sodium Orthosilicate | 4 | 2-3 | 4 | NR |
| Formula #14 | Standard Formula Plus 0.25% Sodium Metasilicate | 1-2 | 4 | 1-2 | NR |
| Formula #15 | Standard Formula Plus 1.0% Monacor 4000 | 1 | 3-4 | 1 | 4 |
| Formula #16 | Standard Formula Plus 0.25% Cobratec TT-50-S | 0-1 | 0-2 | 1-3 | 2-4 |
| Formula #17 | Standard Formula Plus 0.25% Monacor 4000 + 0.25% N Sodium Silicate | 4 | 1-4 | 1 | 1-4 |
| Formula #18 | Standard Formula Plus 0.5% Monacore 4000 + 0.25% N Sodium Silicate | 4 | 1 | 4 | 1 |
| Formula #19 | Standard Formula Plus 0.5% Monacore 4000 + 0.5% N Sodium Silicate | 3 | 1 | 3 | 1 |
| Formula #20 | Standard Formula diluted to 10% concentrate in Tap Water | 1 | NR | 4 | 2 |
| Formula #21 | Standard Formula Plus 0.5% N Sodium Silicate + 0.25% Benzotriazole | 1 | 1 | 0 | 1 |
| Formula #22 | Standard Formula Plus 0.5% N Sodium Silicate + 0.25% 2-mercaptobenzimidazole | 1 | 1 | 0 | 1 |
| Formula #23 | Standard Formula Plus 0.5% N Sodium Silicate + 0.25% 2-mercaptobenzoxazole | 4 | 1 | 1 | 1 |
| Formula #24 | Standard Formula Plus 0.25% Sodium Nitrite | 1-2 | 1-2 | 1 | 3 |

*NR: Not Run
0 - No Visible Corrosion
1 - Very Slight Corrosion or Discoloration (up to 5% of surface area)
2 - Slight Corrosion (5 to 10%)
3 - Moderate Corrosion or Pitting (10 to 25%)
4 - Extensive Corrosion or Pitting (25% or more)

While this invention has been described by a number of specific examples, it is obvious that there are other variations and modifications which can be made without departing from the spirit and scope of the invention as particularly set forth in the appended claims.

The invention claimed is:

1. A process of inhibiting and removing mold, mildew and fungal growth from metal surfaces which comprises treating the metal surfaces with an aqueous solution consisting essentially of:
   (a) from about 0.1 to 3.0 percent by weight of sodium and/or potassium perborate monohydrate;
   (b) from about 0.05 to 5.0 percent by weight of at least one alkali metal silicate;
   (c) a member selected from the group consisting of (i) benzotriazole, tolyltriazole, or a mixture thereof, and (ii) from about 0.1 to 2.0 weight percent of at least one water soluble corrosion inhibitor selected from the group consisting of benzimidazoles, benzazoles, and benzoxazoles; and
   (d) 0.1 to 5.0 percent by weight of at least one water soluble surfactant;

wherein the aqueous solution has a pH ranging from 7.0 to 10, does not include a chlorine bleach, and when component (c)(i) is present in the aqueous solution the combined amount of components (b) and (c)(i) does not exceed about 5.0 weight percent of the solution.

2. The process of claim 1 wherein the surfactant is selected from the group consisting of nonionic, anionic and cationic surfactants.

3. The process of claim 2 wherein the surfactant is a nonionic surfactant.

4. The process of claim 1 wherein component (c)(i) is a mixture of benzotriazole and tolyltriazole.

5. The process of claim 1 wherein the corrosion inhibitor is a mercaptobenzimidazole.

* * * * *